Figure 1:
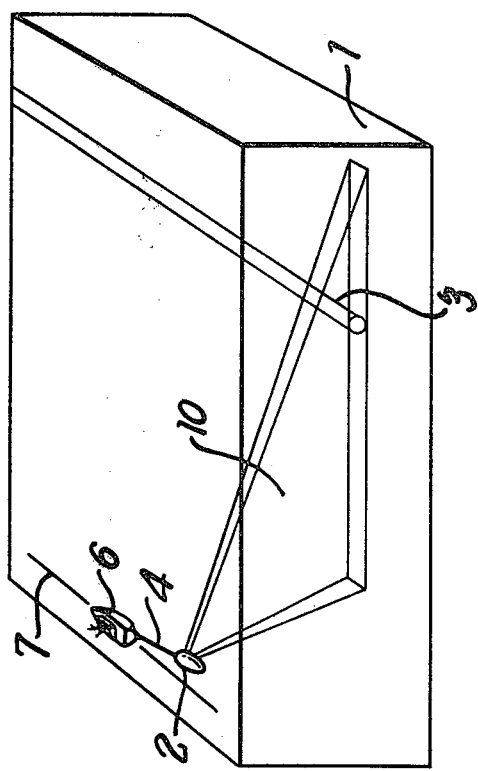

United States Patent [19]
Roberts

[11] 3,992,923
[45] Nov. 23, 1976

[54] UNDERWATER PIPELINES

[75] Inventor: Arthur Roberts, Ashford, England

[73] Assignee: The British Petroleum Company Limited, London, England

[22] Filed: Dec. 1, 1975

[21] Appl. No.: 636,605

Related U.S. Application Data

[63] Continuation-in-part of Ser. No. 539,920, Jan. 9, 1975, which is a continuation-in-part of Ser. No. 420,002, Nov. 29, 1974, abandoned.

[52] U.S. Cl. .......................................... 73/40.5 A
[51] Int. Cl.² ....................................... G01M 3/24
[58] Field of Search ....... 73/40.5 A, 40.5 R, 67.7 R, 73/67.8 R, 19; 340/242

[56] References Cited
UNITED STATES PATENTS

| | | |
|---|---|---|
| 2,997,689 | 8/1961 | Johnson et al. ............... 73/67.7 R X |
| 3,222,635 | 12/1965 | Simpkins et al. ................ 73/40.5 A |
| 3,261,200 | 7/1966 | Long................................. 73/40.5 A |
| 3,289,465 | 12/1966 | Parker ............................ 73/40.5 A |
| 3,409,897 | 11/1968 | Bosselaar et al............ 73/40.5 A X |
| 3,622,958 | 11/1971 | Tucker et al. ...................... 73/19 X |

*Primary Examiner*—Richard C. Queisser
*Assistant Examiner*—Joseph W. Roskos
*Attorney, Agent, or Firm*—Morgan, Finnegan, Pine, Foley & Lee

[57] ABSTRACT

Leaks in gas filled pipelines are detected by moving a transmitter and receiver of ultrasonic pulses externally of the pipeline along a path 100 to 500 feet from the axis of the pipeline, transmitting pulses of 20 to 250 kilohertz and detecting the pulses reflected by gas bubbles with the receiver.

7 Claims, 4 Drawing Figures

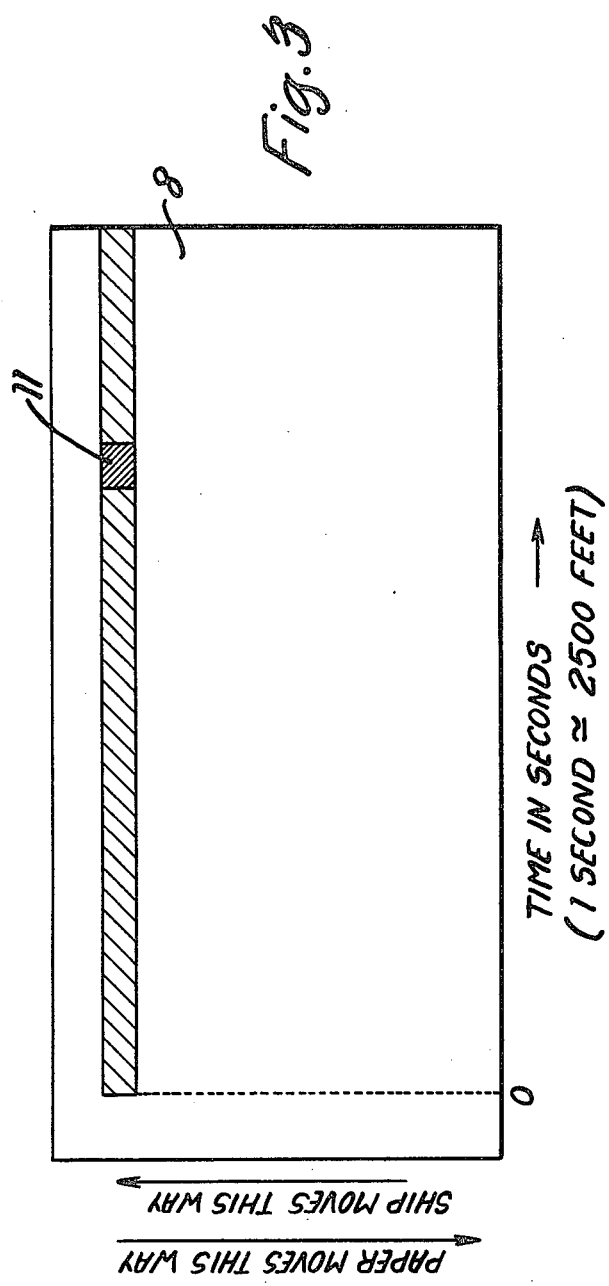
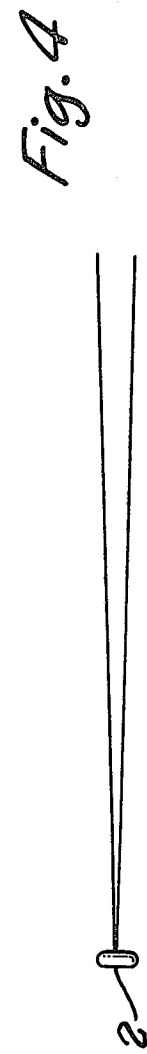

UNDERWATER PIPELINES

This application is a continuation-in-part application of my application Ser. No. 539,920, filed Jan. 9, 1975, a continuation-in-part application of application Ser. No. 420,002, filed Nov. 29, 1974, now abandoned.

This invention relates to a method of testing a gas filled underwater pipeline to detect and locate a leak.

In recent years, underwater pipelines for the transmission of gas and oil have been increasingly employed. It is important that these pipelines should not leak in service since the economic consequences and pollution can be very serious.

A method which has been previously used for detecting a leak in a pipeline before commissioning the pipeline involves filling the pipeline with water under high pressure and detecting any fall in pressure. A fall in pressure will mean that a leak is present but this method does not reveal where the leak is located. There may then follow a time consuming survey of the pipeline by divers.

There is, accordingly, a need for an improved method of locating leaks in underwater pipelines and it is an object of the present invention to provide such a method.

According to the present invention a method of testing an underwater pipeline carrying gas at a greater than ambient pressure to detect whether a leak is present and to locate said leak comprises:

a. moving a transmitter and receiver of ultrasonic pulses externally of the pipeline along a path at a distance of up to 5,000 feet (measured in a horizontal plane) from the axis of the pipeline b. transmitting ultrasonic pulses of frequency in the range 20 to 250 kilohertz at a rate of 0.1 to 10 pulses per second in a beam having a beam width in the horizontal plane of ½ to 10° c. correlating the rate at which pulses are emitted from the transmitter with the speed of movement of the transmitter and receiver, the horizontal beam width and distance of the transmitter and receiver from the axis of the pipeline to detect with the receiver, the pulses reflected by gas bubbles escaping from a leak and thereby detect and locate said leak.

Since the beam referred to in the specification has a finite width, references to the beam making an angle in the present specification refer to the centre of the beam in the plane under consideration.

Preferably the path is from 100 to 1000 feet from the axis of the pipeline, more preferably 200 to 500 feet.

If the speed of movement is too great there is a risk of missing the leak in the interval between consecutive pulses. There is no lower limit on the speed of movement but clearly the lower the speed the longer it will take to detect the leak.

Preferably the speed of movement is less than 12 knots, more preferably from ½ to 10 knots.

The transmitter and receiver of ultrasonic pulses can be moved independently along different paths, although this makes the operation more complicated and they are preferably moved along the same path and more preferably are within 50 feet of each other. The transmitter and receiver can conveniently be attached to the hull of a ship adjacent to each other.

The transmitter and receiver can conveninetly be enclosed in a hollow shell known in the art as a fish and the fish can be towed from a ship by means of a cable.

Suitable transmitters and receivers are disclosed in the British Journal of Applied Physics Vol. 12 March 1961 at pages 103–110.

Such equipment is commercially available and is described in Kelvin Hughes Publication KH entitled "Towed Surveying Asdic".

The transmitter and receiver of ultrasonic pulses can each be a transducer, more preferably the same transducer which can be operated as a receiver during the interval between the transmission of pulses.

Preferably the angle the beam makes with the horizontal is in the range 5° to 25° and the beam width in the horizontal plane is in the range 1° to 2°.

Preferably the beam is transmitted in a direction making an angle of from 85° to 95° with the direction of movement of the transmitter.

Preferably the ultrasonic pulses are of band width of less than 10 kilohertz and more preferably of a single frequency and preferably the frequency is in the range 40 to 150 kilohertz since, within this range, the signal strength from bubbles of escaping gas is normally greater than from other objects in the sea or on the sea bed.

Depending on its design, a transmitter may produce a number of beams simultaneously, a main beam which is preferably the beam employed for the detection, and one or more side lobes.

The receiver, e.g. a hydrophone or transducer preferably converts the acoustic energy into an electrical output which can be amplified and recorded or presented by known means in visual or audible form. Preferably the electrical output is recorded on a "Facsimile" variable intensity paper recorder in conjunction with the movement of the transmitter and receiver along the pipeline to provide a permanent record for inspection.

A hydrophone or transducer usually detects acoustic energy arriving from a wide range of directions and will be sensitive to background acoustic energy due to the ship or water movements. This background acoustic energy may make it difficult to distinguish the signal strength from bubbles of escaping gas. It is, therefore, preferred to use a directional hydrophone e.g. transducer, which is sensitive only to energy coming from the direction of the pipeline. The theory and construction of directional hydrophones is well known.

Preferably the receiver is capable of receiving pulses mainly within an arc of 10° measured in a horizontal plane, more preferably an arc of 2°, and mainly within an arc of 20° measured in a vertical plane, more preferably an arc of 10°.

Preferably the receiver is arranged to be sensitive to frequencies of ± 25% of the frequency transmitted from the transmitter, more preferably of ± 10% of the frequency transmitted.

If the interval between pulses is too short there is a risk of interference between consecutive pulses and if the interval is too long there is a risk of failing to detect the leak.

Preferably the duration of each pulse is about 0.2 to 1.0 milliseconds.

Preferably the pulses are transmitted at a rate in the range 0.5 to 4 pulses per second.

Preferably the pressure of gas inside the pipeline is in the range 50 to 3000 psi above ambient, more preferably 500 to 2500 psi above ambient under which conditions a readily detectable quantity of bubbles is normally produced.

When the depth of water in which the pipeline lies is greater than 200 feet, the transmitter and receiver of ultrasonic pulses are preferably moved along a path within the range 20 to 120 feet, more preferably 50 to 100 feet, of the water bottom, since the sensitivity of the method is sometimes adversely affected by temperature gradients in the water.

Whilst the present invention provides a method of detecting and locating a leak, it can be conveniently employed as a routine testing procedure when there is no reason to suspect the presence of a leak. Also if a leak is already known to be present, e.g. by loss of pressure, the invention can be used to locate the leak.

In a preferred embodiment of the invention a method of testing an underwater pipeline carrying gas at a greater than ambient pressure to detect a leak and to locate said leak comprises pressuring the pipeline with gas to a pressure in the range 50 to 3000 psi above the ambient pressure, moving the transmitter and receiver along a path substantially parallel to the axis of the pipeline at a speed of less than 12 knots and transmitting the beam of ultrasonic pulses at a rate of 0.5 to 4 pulses per second and at an angle of from 85° to 95° with the direction of movement of the transmitter and at a frequency in the range 40 to 150 kilohertz, and employing a receiver capable of detecting frequencies only in the range 75 to 125% of the frequency transmitted.

EXAMPLE

Figure 2:
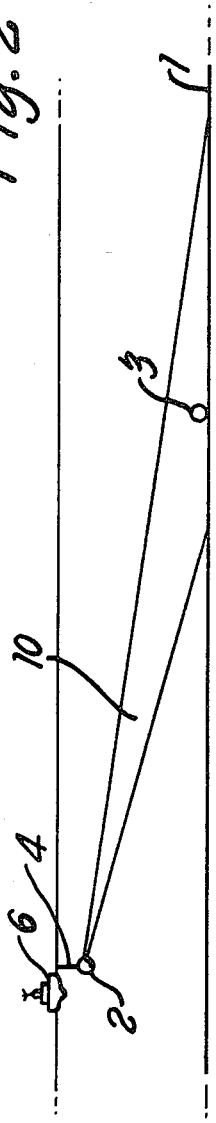

An example of the invention is illustrated by the accompanying drawings in which FIG. 1 is a perspective view of the method showing a ship towing a transmitter and receiver. The upper part of FIG. 2 is a side elevation showing the transmitted and reflected pulses. FIG. 3 shows the recording and FIG. 4 is a plan view showing the transmitted beam of pulses.

A pipeline 3 having an internal diameter of 3½ inches and lying on the sea bed 1 under 85 feet of water was pressured with air at 200 psia. A transmitter and receiver of ultrasonic pulses in the form of a Kelvin Hughes magnetostrictive transducer enclosed in a fish 2 was towed by means of a cable 4 from a ship 6 along a path 7 parallel to the axis of the pipeline at a depth of 15 feet ie.. 70 feet above the sea bed 1 at a speed of 4 knots. Ultrasonic pulses were transmitted at a frequency of 50 kilohertz at a rate of 2 pulses per second in a beam 10 whose width in the horizontal plane was 1½° and the beam made an anle of 10° with the horizontal, and was transmitted at 90° to the direction of movement. The path 7 was 550 feet to the left hand side of the pipeline and parallel to the axis of the pipeline 3. The transducer acted as a directional receiver (capable of receiving pulses only within an arc of 1.5° in a horizontal plane and 10° in the vertical plane) in the interval between transmitting pulses.

The pulses received by transducer were amplified in known manner and recorded on a variable intensity paper recorder 8.

A leak was detected by a strong signal 11 returned from the stream of bubbles emanating from the leak in the pipeline.

I claim:
1. A method of testing an underwater pipeline carrying gas at a greater than ambient pressure to detect whether a leak is present and to locate said leak which method comprises:
   a. moving a transmitter and receiver of ultrasonic pulses externally of the pipeline along a path at a distance of up to 5,000 feet (measured in a horizontal plane) from the axis of the pipeline
   b. transmitting ultrasonic pulses of frequency in the range 20 to 250 kilohertz at a rate of 0.1 to 10 pulses per second in a beam having a beam width in the horizontal plane of ½ to 10°
   c. correlating the rate at which pulses are emitted from the transmitter with the speed of movement of the transmitter and receiver, the horizontal beam width and distance of the transmitter and receiver from the axis of the pipeline to detect with the receiver, the pulses reflected by gas bubbles escaping from a leak and thereby detect and locate said leak.

2. A method as claimed in claim 1 wherein the transmitter and receiver are moved along a path in the range 100 to 1000 feet from the axis of the pipeline.

3. A method as claimed in claim 1 wherein the beam makes an angle of 2° to 45° with the horizontal and an angle of 70° to 110° (measured in the horizontal plane) with the direction of movement of the transmitter.

4. A method as claimed in claim 1 wherein the ultrasonic pulses are transmitted so that the pipeline is within the beam of pulses.

5. A method as claimed in claim 1 wherein a single transducer is both the transmitter and receiver of ultrasonic pulses and the transducer is operated as a receiver in the interval between transmitting pulses.

6. A method as claimed in claim 1 wherein the pipeline is pressurised with gas to a pressure in the range 50 to 3,000 psi above the ambient pressure, the transmitter and receiver are moved along a path substantially parallel to the axis of the pipeline at a speed of less than 12 knots and the beam of ultrasonic pulses is transmitted at a rate of 0.5 to 4 pulses per second and at an angle of from 85° to 95° with the direction of movement of the transmitter and at a frequency in the range 30 to 150 kilohertz, the receiver is arranged to be capable of detecting frequencies only in the range 75 to 125% of the frequency transmitted.

7. A method as claimed in claim 1 wherein when the depth of water in which the pipeline is greater than 200 feet, the transmitter and receiver of ultrasonic pulses are moved along a path within the range 20 to 120 feet of the water bottom.

* * * * *